(12) United States Patent
Pekonen et al.

(10) Patent No.: US 10,126,427 B2
(45) Date of Patent: Nov. 13, 2018

(54) ESTIMATING LOCAL MOTION OF PHYSICAL EXERCISE

(71) Applicant: POLAR ELECTRO OY, Kempele (FI)

(72) Inventors: Elias Pekonen, Oulu (FI); Jari Miettinen, Oulu (FI); Ville Majava, Kiviniemi (FI); Antti Taini, Oulu (FI); Markus Laapotti, Oulu (FI)

(73) Assignee: Polar Electro Oy, Kempele (FI)

( * ) Notice: Subject to any disclaimer, the term of this patent is extended or adjusted under 35 U.S.C. 154(b) by 642 days.

(21) Appl. No.: 14/464,343

(22) Filed: Aug. 20, 2014

(65) Prior Publication Data

US 2016/0054449 A1 Feb. 25, 2016

(51) Int. Cl.
| | | |
|---|---|---|
| *G01S 19/19* | (2010.01) | |
| *A63B 24/00* | (2006.01) | |
| *G01S 19/49* | (2010.01) | |
| *A61B 5/11* | (2006.01) | |
| *G01C 25/00* | (2006.01) | |

(Continued)

(52) U.S. Cl.
CPC .......... *G01S 19/19* (2013.01); *A61B 5/1112* (2013.01); *A63B 24/0003* (2013.01); *A63B 24/0062* (2013.01); *G01C 22/006* (2013.01); *G01C 25/005* (2013.01); *G01S 19/49* (2013.01);

(Continued)

(58) Field of Classification Search
CPC .......... A61B 5/681; A61B 5/02; A61B 5/024; A61B 5/021; A61B 5/103; A61B 5/11; A61B 5/1112; A61B 5/68; A61B 5/6801; A61B 5/6802; A61B 5/0205; A61B 2505/09; G01C 22/006; G01C 22/005; G01S 19/01; G01S 19/13; G01S 19/14; G01S 19/19; G01S 19/38; G01S 19/39; G01S 19/42; G01S 19/48; G01S 19/49; G06K 9/00335; G06K 9/00342;

(Continued)

(56) References Cited

U.S. PATENT DOCUMENTS

| | | | |
|---|---|---|---|
| 5,926,131 A | | 7/1999 | Sakumoto et al. |
| 6,009,375 A | * | 12/1999 | Sakumoto ............ G01C 22/006 |
| | | | 342/357.57 |

(Continued)

FOREIGN PATENT DOCUMENTS

| | | | |
|---|---|---|---|
| EP | 2 505 238 A1 | 10/2012 | |
| FR | 2885531 A1 | * 11/2006 | ......... A63B 24/0003 |

OTHER PUBLICATIONS

European Search Report, Application No. EP 15 17 9768, 2 pages, dated Jan. 7, 2016.

*Primary Examiner* — Bernarr E Gregory
(74) *Attorney, Agent, or Firm* — FisherBroyles, LLP

(57) ABSTRACT

A solution for estimating motion of a user is disclosed. A method comprises: acquiring satellite positioning data received with a satellite positioning receiver attached to a human body and indicating a location of the satellite positioning receiver; extracting, from the satellite positioning data, local motion data representing local motion of the satellite positioning receiver with respect to a reference point and overall motion data representing the motion of the reference point, wherein the reference point is included in a framework of the human body; and determining, from the local motion data, a local motion trajectory of a part of a human body to which the satellite positioning receiver is attached with respect to the reference point.

27 Claims, 7 Drawing Sheets

(51) Int. Cl.
  *G01C 22/00*  (2006.01)
  *A61B 5/00*  (2006.01)
  *A61B 5/024*  (2006.01)
  *G01S 19/00*  (2010.01)

(52) U.S. Cl.
  CPC ............... *A61B 5/024* (2013.01); *A61B 5/681* (2013.01); *A61B 2505/09* (2013.01)

(58) Field of Classification Search
  CPC ............ G06K 9/00348; G06K 9/00355; A63B 24/0003; A63B 24/0006; A63B 24/0062
  See application file for complete search history.

(56) References Cited

U.S. PATENT DOCUMENTS

| | | | |
|---|---|---|---|
| 6,285,314 B1 | 9/2001 | Nagatsuma et al. | |
| 6,522,266 B1* | 2/2003 | Soehren | G01S 19/49 340/988 |
| 6,532,432 B1 | 3/2003 | Nagatsuma et al. | |
| 8,187,182 B2* | 5/2012 | Kahn | A61B 5/1112 482/1 |
| 9,041,600 B2* | 5/2015 | Papagerogiou | G01C 22/006 342/357.23 |
| 2005/0033200 A1* | 2/2005 | Soehren | A61B 5/1112 600/595 |
| 2007/0250261 A1* | 10/2007 | Soehren | G01C 22/006 701/510 |
| 2012/0200455 A1 | 8/2012 | Papagerogiou | |
| 2012/0231840 A1* | 9/2012 | Calman | G06K 9/00342 455/556.1 |

* cited by examiner

ESTIMATING LOCAL MOTION OF PHYSICAL EXERCISE

BACKGROUND

Field

The present invention relates to motion estimation and, particularly, estimating local motion of a user during a physical exercise.

Description of the Related Art

There exist some commercial solutions for estimation local motion of a user during a physical exercise. The local motion may refer to motion of an arm or a leg or another part of a human body with respect to overall motion of the human body, e.g. motion of a centre of mass of the human body. The local motion is typically measured and estimated by using motion sensors such as accelerometers and gyroscopes.

SUMMARY

According to an aspect, there is provided a method comprising: acquiring, in an apparatus, satellite positioning data received with a satellite positioning receiver attached to a human body and indicating a location of the satellite positioning receiver; extracting, by the apparatus from the satellite positioning data, local motion data representing local motion of the satellite positioning receiver with respect to a reference point and overall motion data representing the motion of the reference point, wherein the reference point is comprised in a framework of the human body; and determining, from the local motion data, a local motion trajectory of a part of a human body to which the satellite positioning receiver is attached with respect to the reference point.

According to another aspect, there is provided an apparatus comprising at least one processor and at least one memory including a computer program code. The at least one memory and the computer program code are configured, with the at least one processor, to cause the apparatus to: acquire satellite positioning data received with a satellite positioning receiver attached to a human body and indicating a location of the satellite positioning receiver; extract, from the satellite positioning data, local motion data representing local motion of the satellite positioning receiver with respect to a reference point and overall motion data representing the motion of the reference point, wherein the reference point is comprised in a framework of the human body; and determine, from the local motion data, a local motion trajectory of a part of a human body to which the satellite positioning receiver is attached with respect to the reference point.

According to yet another aspect, there is provided a computer program product embodied on a distribution medium readable by a computer and comprising program instructions which, when loaded into an apparatus, execute a computer process comprising: acquiring satellite positioning data received with a satellite positioning receiver attached to a human body and indicating a location of the satellite positioning receiver; extracting, from the satellite positioning data, local motion data representing local motion of the satellite positioning receiver with respect to a reference point and overall motion data representing the motion of the reference point, wherein the reference point is comprised in a framework of the human body; and determining, from the local motion data, a local motion trajectory of a part of a human body to which the satellite positioning receiver is attached with respect to the reference point.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
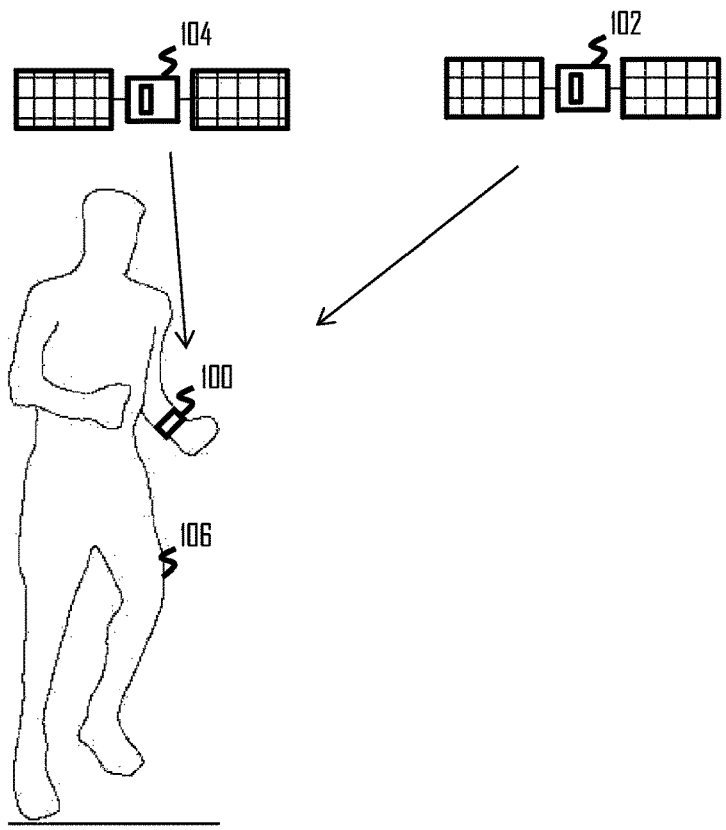
FIG. 1 illustrates a scenario to which embodiments of the invention may be applied.

FIG. 1 illustrates a physical training scenario to which embodiments of the invention may be applied. Referring to FIG. 1, a user 106 may be carrying out a physical exercise such as running, walking, playing a sports game, training for some sports type, etc. The user 106 may be wearing a training computer 100 such as a wrist computer. The user may, additionally, or alternatively, wear one or more training computers attached to determined locations in his/her body. Commonly known training computers include, in addition to the wrist computer, a foot-worn training computer arranged to measure motion of a foot, a heart rate transmitter worn attached to the chest, a torso-worn training computer attached to the torso and arranged to measure motion of the torso, an arm-worn training computer attached to the upper arm, etc. One of the training computers may comprise a satellite positioning receiver arranged to receive signals from positioning satellites 102, 104 and to compute positioning coordinates of the satellite positioning receiver. The satellite positioning receiver may support positioning based on Global Positioning System, Galileo positioning system, Global Navigation Satellite System (GLONASS), etc.

Modern satellite positioning systems and satellite positioning receivers have been developed to provide high accuracy positioning. Furthermore, the measuring frequency of the satellite positioning receivers is sufficient to measure relatively rapid momentary motion of the user 100. For example, some commercially available satellite positioning sensors employ a measuring frequency of 10 Hertz (Hz). As a result of this development, it is possible to use the satellite positioning receiver to acquire satellite positioning data and to estimate local motion of the user 106 from the satellite positioning data. According to the known Nyquist criterion, a sampling frequency of the above-mentioned 10 Hz enables detection of changes having the highest frequency component of 5 Hz which, in the context of the human local motion, is sufficient for detecting the motion of the arm or foot, for example.

Figure 2:
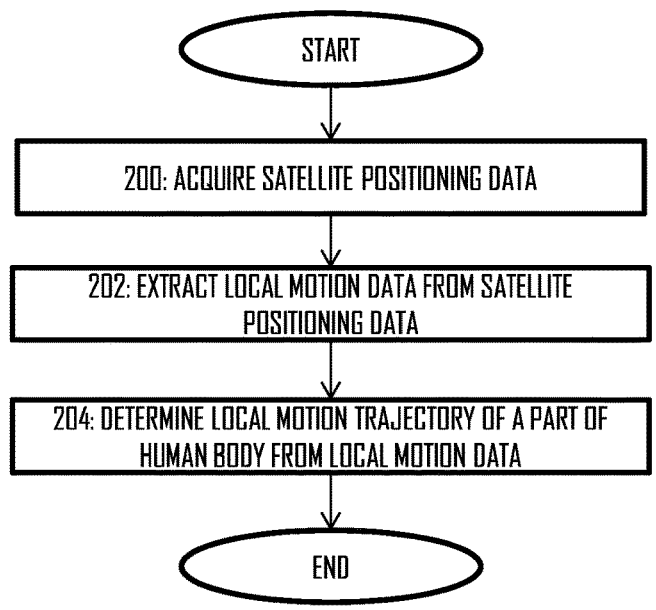
FIG. 2 illustrates a flow diagram of a process for estimating local motion from satellite positioning data according to an embodiment of the invention.

FIG. 2 illustrates a process for estimating local motion of the user 106. The process of FIG. 2 may be executed in a training computer attached to the user 106 and connected to the satellite positioning receiver, or it may be executed in a server computer to which the satellite positioning data is transferred from the satellite positioning receiver during the physical exercise or after the physical exercise. Referring to FIG. 2, the process comprises acquiring, in an apparatus, satellite positioning data received with a satellite positioning receiver and indicating a location of the satellite positioning receiver (block 200). The apparatus extracts from the satellite positioning data local motion data representing local motion of the satellite positioning receiver with respect to a reference point and overall motion data representing the motion of the reference point (block 202). The reference point may be a point attached to the user's 106 body or to a framework of the user's 106 body. The framework may refer to the user's body or to an object attached to the user's body. The object may be sports equipment such as a bicycle, a ski pole, a ski, an apparel, or even a vehicle. The framework may be any object so attached to the user's body that the overall motion of the user 106 may be derived from the motion of the framework. The apparatus then determines from the local motion data a local motion trajectory of a part of a human body to which the satellite positioning receiver is attached with respect to the reference point (block 204).

In an embodiment, the part of the human body associated with the measured local motion is the part to which a training computer comprising the satellite positioning receiver is arranged to be attached, e.g. the arm, leg, foot, or limb of the human body. In an embodiment, the part of the human body may be determined from the local motion data, e.g. whether the local motion data represents local motion trajectories that are known to by typical for the arm or the foot.

Figure 3A:
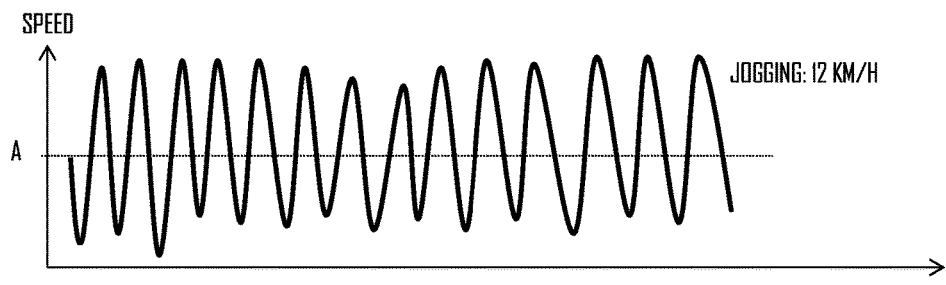
FIGS. 3A to 3C illustrate examples of satellite positioning data measured in connection with different sports types.
Figure 3B:
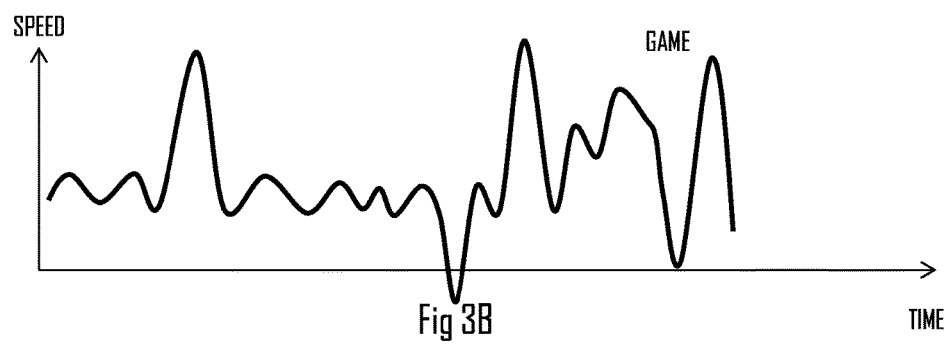
Figure 3C:
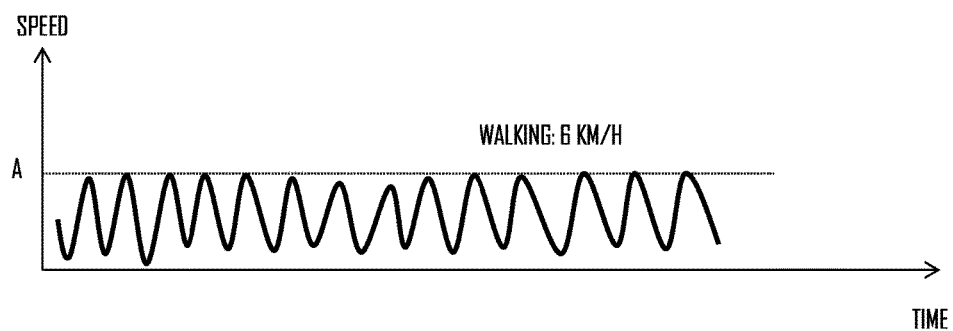

FIGS. 3A, 3B, and 3C illustrate satellite positioning data in the form of raw speed data computed from the satellite positioning data. The raw speed data may refer to that no averaging has been applied when computing the speed data or that an averaging window is short with respect to averaging window applied when computing speed data displayed to the user 106 through a user interface of the training computer, e.g. the wrist computer. Let us assume that the satellite positioning receiver is attached to the same part in the user's 106 body in FIGS. 3A to 3C and, as a consequence, FIGS. 3A to 3C illustrate the motion of that part when performing different types of physical exercises. The part may be an arm or a wrist of the user 106. FIG. 3A illustrates the speed data in connection with running at constant speed, e.g. when jogging. As illustrated in FIG. 3A, the speed data acquired from the satellite positioning data is highly periodic and represents the form of a sine wave. Another typical characteristic of the speed data is high variance of the speed around an average level represented by 'A'. FIG. 3B illustrates the speed data when playing a game such as badminton. As illustrated in FIG. 3B, the speed data acquired from the satellite positioning data is not very stationary in terms that the variance of the speed data is high, and no periodicity or a regular pattern can be found. FIG. 3C the speed data when walking. The pattern of the speed data is similar to that of running except that the variance of the speed data around the average level is smaller and the average level of the speed is lower than the average level 'A' of the running. As shown in FIGS. 3A to 3C, satellite positioning data may provide motion data similar to that acquired by using other motion sensors such as an accelerometer, gyroscope, and magnetometer. An advantage of the satellite positioning data is that it is inherently fixed to determined coordinates associated with the satellite positioning system employed by the satellite positioning receiver. Accordingly, the satellite positioning data is readily calibrated, thus overcoming one problem of the other types of motion sensors.

Figure 4A:
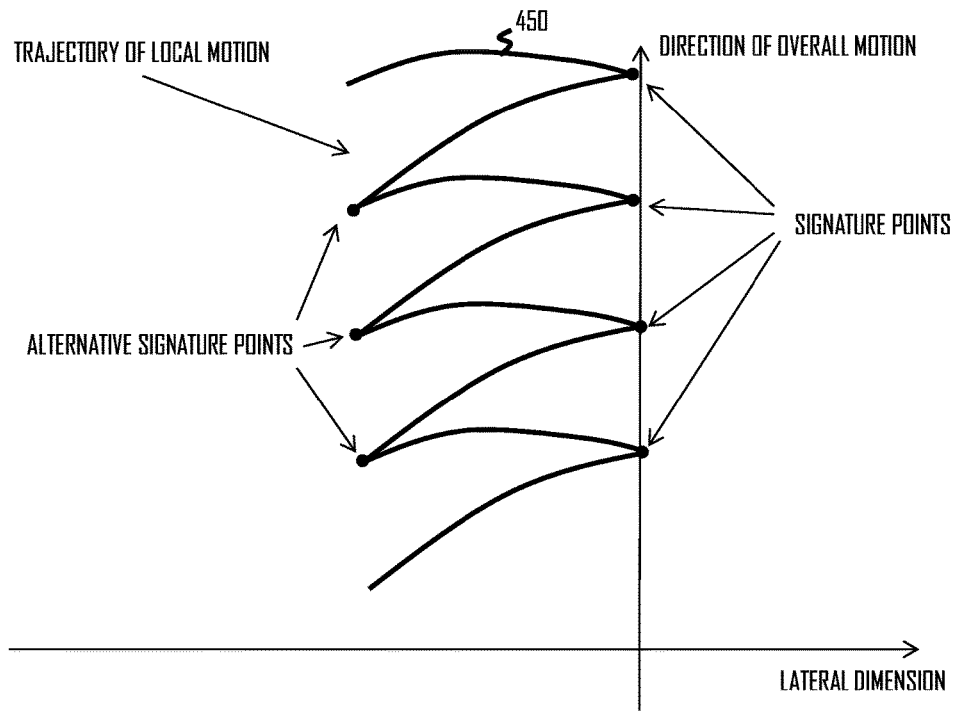
FIG. 4A illustrates local motion and overall motion in spatial coordinates.
Figure 4B:
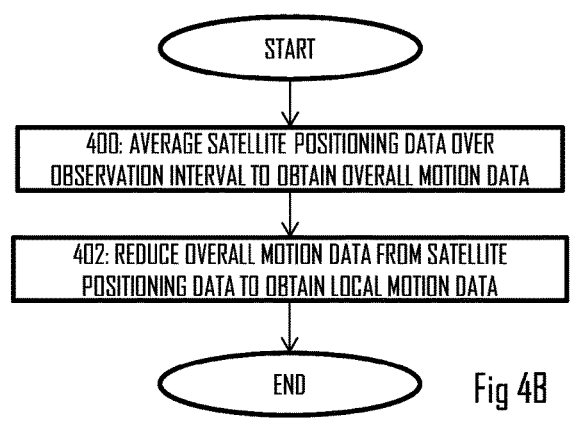
FIGS. 4B and 4C illustrate processes for extracting local motion data and overall motion data from satellite positioning data according to some embodiments of the invention.
Figure 4C:
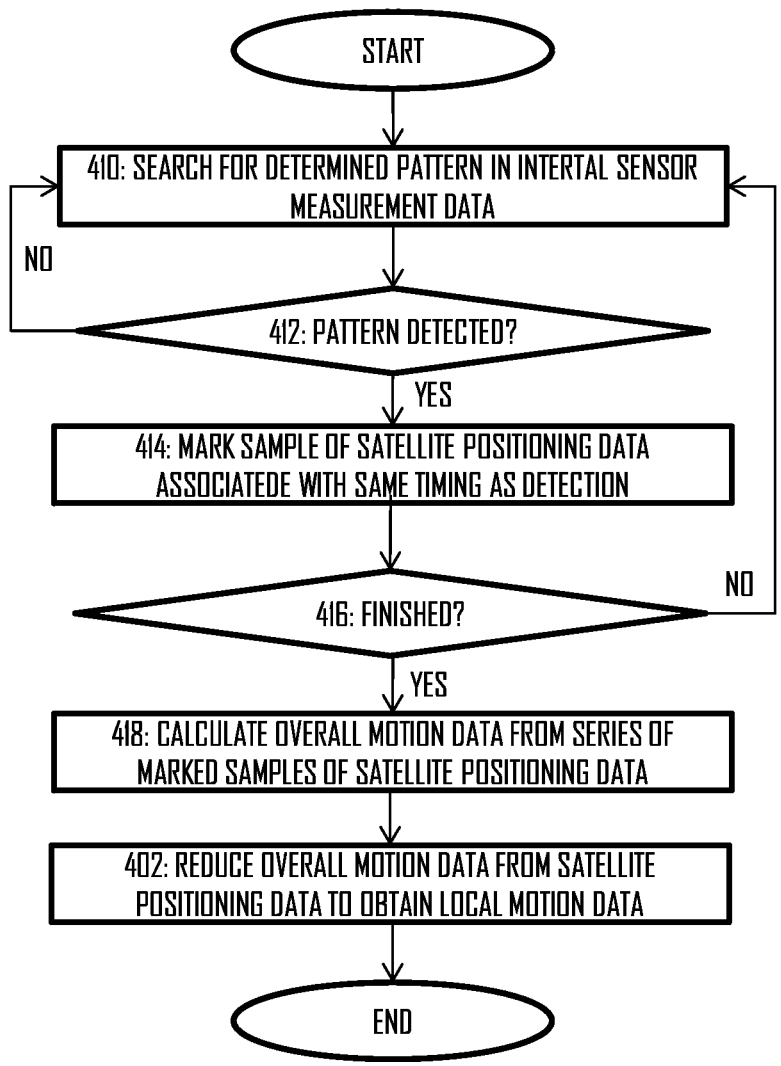

Let us now consider some embodiments for processing the satellite positioning data. FIG. 4A illustrates motion trajectories of the overall motion and the local motion in spatial coordinates when the user carries a repetitive exercise such as running of walking. As shown in FIG. 4A, the overall motion represents the direction to which the human body or the framework of the human body moves or, in other words, a general direction to which the graph 450 of FIG. 4A progresses. The local motion represents back-and-forth motion of an arm, for example. FIGS. 4B and 4C illustrate some embodiments for extracting the overall motion data and the local motion data from the satellite positioning data. Referring to FIG. 4, the overall motion is represented by a signal component that models general propagation of the graph. This signal component may be extracted from an average motion trajectory of the graph of from a motion trajectory formed by selected signature points of the graph. The signature may be considered to refer to a unique property of the graph that repeats with a determined periodicity. The property may be a lateral turning point of the trajectory from a lateral direction to another, opposite lateral direction, as illustrated as signature points in FIG. 4A, or from the other opposite lateral direction to said lateral direction. As shown in FIG. 4, the interval between consecutive signature points or between consecutive alternative signature points represents one period, and the signature points taken into consideration in determining the direction of the overall motion may be distributed with one period intervals. As shown in FIG. 4A, a graph drawn by a series of signature points or a graph drawn by a series of alternative signature points both provide the same graph which represents the direction of the overall motion.

FIG. 4B illustrates an embodiment for extracting the overall motion data and the local motion data from the satellite positioning data. The satellite positioning data may be positioning coordinates or speed data measured by the satellite positioning receiver. Referring to FIG. 4B, the overall motion data is acquired by averaging (in block 400) the satellite positioning data over an observation interval. The local motion data is acquired by subtracting the overall motion data from the satellite positioning data in block 402. The overall motion data may represent the average component illustrated in FIG. 3A, for example. The overall motion data may represent the motion of the user 106 as a whole or the motion of the mass centre of the user 106. The local motion data may represent the motion of the satellite positioning receiver with respect to the torso or the mass centre of the user 106.

FIG. 4C illustrates another embodiment for extracting the overall motion data and the local motion data from the satellite positioning data. The satellite positioning data may be positioning coordinates or speed data measured by the satellite positioning receiver. Referring to FIG. 4C, the overall motion data is acquired by detecting the above-described signature points in the satellite positioning data and computing the overall motion data from a series of detected signature points. In block 410, the signature points are detected by employing an inertial sensor arranged to measure acceleration caused by the motion of the user 106. The inertial sensor may comprise an accelerometer and/or a gyroscope, for example. Referring back to FIG. 4A, each signature point is associated with a specific pattern in the inertial measurement data provided by the at least one inertial sensor. The pattern may be a turning point in acceleration, a minimum acceleration value, or a maximum acceleration value, for example, and such a pattern is monitored for in block 410. In block 412, it is determined whether or not the pattern is detected in the inertial sensor measurement data. If the pattern has not been detected, the process may return to block 410. If the pattern has been detected, the process may proceed to block 414 in which a sample of the satellite positioning data measured at the same time as the pattern was detected is marked. Accordingly, the decision "YES" in block 412 may cause time-stamping the corresponding sample of the satellite positioning data. In block 416, it is determined whether or not more signature points are needed. If yes, the process may return to block 410. In an embodiment, a plurality of signature points is needed for computing the overall motion data. If the process is ready for computing the overall motion data in block 416, the process may proceed to block 418 in which the overall motion data is computed from the series of marked samples of the satellite positioning data. Block 418 may comprise estimating a trajectory formed by the marked samples of the overall motion data. The trajectory may be formed by fitting the marked samples to a determined graph. Such fitting may be performed by employing state-of-the-art matching algorithms such as least squares matching. The overall motion data may then be reduced from the satellite positioning data in the above-described manner in block 402.

In an embodiment alternative to block 410 of FIG. 4C, the determined pattern may be searched from the satellite positioning data. When block 410 is modified in such a manner, the inertial sensor may not be needed in the execution of the process of FIG. 4C.

Figure 5:
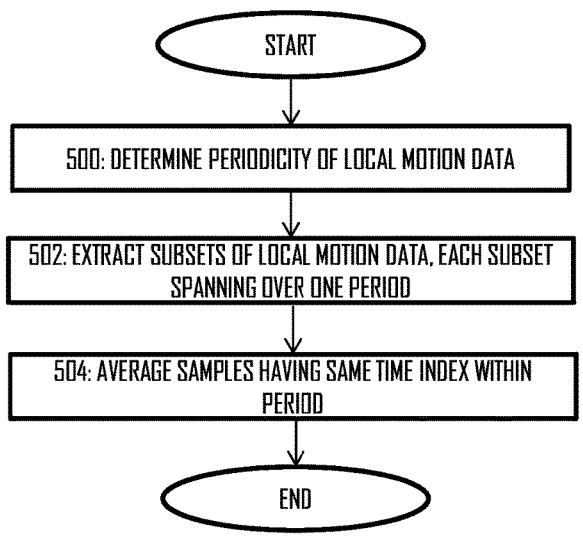
FIG. 5 illustrates averaging performed according to an embodiment of the invention.

As described above, the overall motion data may be acquired by averaging samples of the satellite positioning data over a determined observation interval. Another type of averaging may be applied to average the local motion data, as described next with reference to FIGS. 5 and 6. When the user 106 performs a repetitive exercise such as running, walking, cycling, or swimming, the motion is periodic. The periodic motion may be utilized in the averaging process when estimating technical performance of the exercise, for example. FIG. 5 illustrates a flow diagram of a process for improving performance of local motion estimation according to an embodiment of the invention. The process of FIG. 5 may be executed in the above-mentioned apparatus. Referring to FIG. 5, the process comprises determining periodicity of the local motion data in block 500. In an embodiment, block 500 comprises determining whether or not the local motion data is periodic and, if determined to be periodic, the length of a period. The periodicity may be determined by applying an autocorrelation check to the local motion data. The autocorrelation check may be performed by using a plurality of autocorrelation window lengths in order to determine the length of the autocorrelation window with which the local motion data is determined to correlate with itself. If the local motion data is found to correlate with itself with a given autocorrelation window such that a correlation peak resulting from the autocorrelation function exceeds a threshold, the local motion data may be determined to be periodic and the length of the period is the length of the autocorrelation window.

Figure 6:
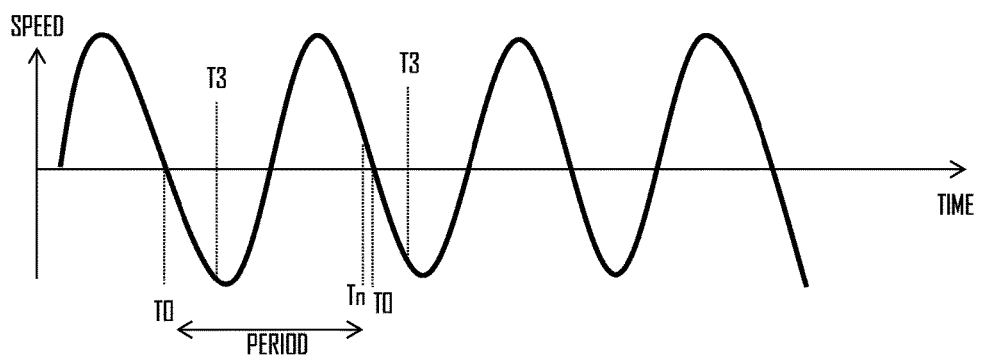
FIG. 6 illustrates how samples of the local motion data are averaged in the embodiment of FIG. 5.

When the period of the periodic local motion has been determined in block 500, the local motion data may be divided into a plurality of subsets, wherein each subset represents local motion data over one period (block 502). Each of the subsets may contain local motion data of a different period. Each sample in each subset may be associated with a time index or the samples may be otherwise ordered in the same order as they have been measured. Each subset may contain the same number of samples. In block 504, averaging over the subsets is performed such that samples having the same time index in different subsets are averaged. In this manner the samples representing the same local motion in the periodic local motion data are averaged and, as a consequence, the averaging is performed over a plurality of repetitions of the same local motion. Referring to FIG. 6 illustrating the periodic speed data of FIG. 3B, let us assume that the speed data has already been averaged over an observation interval and the overall motion data (an average speed) has been subtracted from the speed data. This is shown by the speed data being scaled around the horizontal time axis. In other words, the speed data in FIG. 6 represents the speed of the local motion. As shown and described above, the local motion is found to be periodic with the period illustrated in FIG. 6. The period may span from sample T0 to Tn and, as a consequence, the local motion data is divided into subsets, each subset comprising local speed data samples having time indices from T0 to Tn. In block 504, the local speed samples having time index T0 are averaged together, the local speed samples having time index T1 are averaged together, and so on until time index Tn. This type of averaging may improve the estimation of the average local motion which may represent better an average motion technique of the user 106 in running or swimming, for example.

Let us now consider some embodiments for employing the local motion data acquired from the satellite positioning data when processing measurement data acquired during the exercise. In an embodiment illustrated in FIG. 7, the local motion data is used in determining the length of an averaging window applied when computing overall speed during the physical exercise. As known in the art, the speed may be computed from coordinates of the satellite positioning data by using an averaging window that is conventionally used to reduce the effect of inaccuracies in the satellite positioning. A long averaging window causes a delay in the processing which shows in delayed response in a speed value illustrated to the user 106 during the exercise. In some sports types where the speed remains relatively constant, such as jogging or walking, the delay does not degrade the use experience and a long averaging window may be applied. In other sports types such as cross-country skiing, alpine skiing, or cycling where the motion may be spurious, a short averaging window is preferred so that the displayed speed reacts faster to the rapid changes in the speed.

Figure 7:
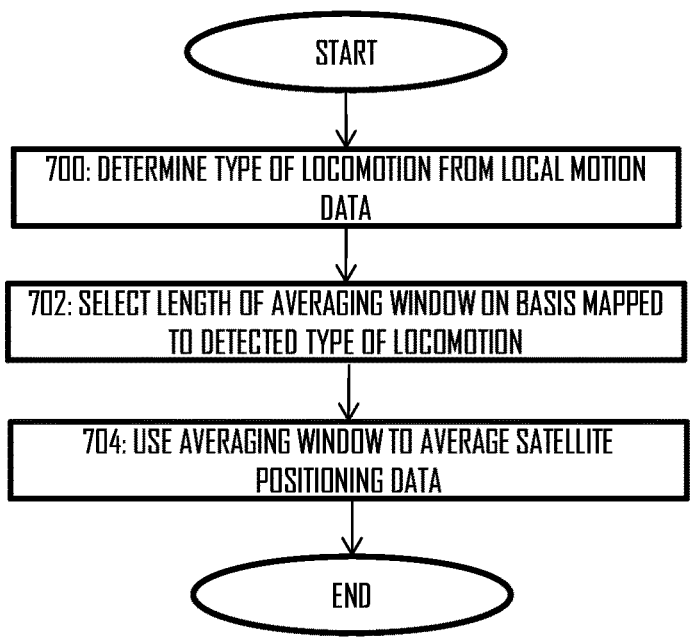
FIG. 7 illustrates a process for configuring processing functions according to a sports type determined from satellite positioning data according to an embodiment of the invention.

Referring to FIG. 7, the process comprises determining a type of locomotion from the local motion data in block 700. In an embodiment, the type of locomotion is the sports type and determining the type of locomotion comprises determining the sports type. The type of locomotion may be determined by analysing characteristics of at least the local motion data. In some embodiments, characteristics of the local motion data and the overall motion data may be used to determine the type of locomotion. The local motion data may be acquired in the above-described manner by subtracting the overall motion data from the satellite positioning data or by scaling the satellite positioning data with the overall motion data. The scaling may be carried out by dividing the satellite positioning data with the overall motion data acquired by averaging the satellite positioning data. Selected one or more characteristics of the local motion data may be computed in block 700. In an embodiment, block 700 comprises computing a standard deviation or variance of the local motion data. The standard deviation or variance may be computed over an observation interval which may be eight, ten, or 20 consecutive samples of the local motion data, for example. The standard deviation or the variance may then be compared with a threshold. If the threshold is exceeded in the comparison, the type of locomotion is determined to be periodic or rhythmic such as jogging or walking. If the threshold is not exceeded, the sports type is determined to be aperiodic or spurious such as football or another team sports, badminton, tennis, etc.

In an embodiment, the determination of the type of locomotion in block 700 comprises making a selection between a periodic type of locomotion and an aperiodic type of locomotion.

In an embodiment, the determination of the type of locomotion in block 700 comprises determining what sports the user is performing. This may comprise making a selection of the sports type amongst a set of sports types comprising a subset of the following sports types: walking, running, cycling, swimming, and cross-country skiing.

When the type of locomotion has been determined in block 700, the determined sports type may be used in determining as how to process the measurement data. In the embodiment of FIG. 7, the length of the averaging window applied to the measurement data is selected on the basis of the detected type of locomotion. For example, each type of locomotion may be mapped to a determined length of the averaging window in a mapping table employed by the apparatus, and the averaging window is selected in block 702 by selecting an averaging window mapped to the type of locomotion determined in block 700. Then, the selected averaging window is used when averaging measurement data to acquire speed data, for example. In an embodiment, the measurement data is the satellite positioning data.

In an embodiment of FIG. 7, the type of locomotion is determined in a refined manner by employing further analysis in block 700. For example, if the local motion data is determined to exceed the threshold, the overall motion data may then be analysed to determine what type of periodic or rhythmic locomotion is being performed. For example, a speed value may be computed from the overall motion data. If the speed matches to a speed range associated with running, the type of locomotion may be determined to be running. If the speed matches to a speed range associated with walking, the type of locomotion may be determined to be walking.

In an embodiment of block 700, the type of locomotion is determined from the periodicity of the local motion data. If the local motion data is determined to be periodic, the longer averaging window may be selected in block 702. If the local motion data is determined to have no periodicity, the shorter averaging window may be selected in block 702. Another embodiment employs the periodicity to compute various characteristics of the motion. For example, the periodicity of the local motion data may be a direct indicator of a cadence of walking, running, cycling, cross-country skiing, or swimming. As the step cadence may be estimated in this manner, a running index proportional to the step cadence may be determined. The running index may give information about the performance level of the user 106, both aerobic fitness and running economy. Similarly, a step count during the exercise may be computed from the periodicity of the local motion data. In yet another embodiment, step length may be computed from the determined length of the period $t_p$ and the overall speed data $v_o$ during the period. The period may represent the duration of two steps, e.g. when the satellite positioning receiver is attached to the arm or foot of the user 106. The step length $s_s$ may be computed by employing the well-known equation $s_s = t_p * v_o / 2$.

In yet another embodiment of block 700, the type of locomotion is determined from a local motion trajectory derived from the local motion data. The apparatus may store a reference trajectory database storing parameters for reference trajectories associated with each type of locomotion the apparatus is capable of identifying. The acquired local motion data may be correlated with each reference motion trajectory until a match between the local motion data and one of the reference motion trajectories is detected. A type of locomotion associated with the reference motion trajectory matching with the local motion data may be selected as the determined type of locomotion. Similar to what has been described above, the cadence and the step/stroke length may be determined on the basis of the trajectory analysis. A motion trajectory associated with a step or a stroke may be extracted from the local motion data by comparing the local motion data with a reference motion trajectory of a step or a stroke. Upon extracting samples representing the motion trajectory associated with the step or a stroke or a plurality of steps or strokes, a time interval associated with the samples may be determined and the cadence is acquired by mapping the resulting value to a determined time scale, e.g. steps/strokes per minute. The step/stroke length may be derived from the cadence and a travelled distance acquired from the overall motion data by dividing the distance travelled within a determined time interval by the cadence scaled to the same time interval.

The reference motion trajectories may be stored in the reference trajectory database as motion trajectory values in two-dimensional or three-dimensional coordinates. The motion trajectory values may be location values or speed values, for example. Table 1 below illustrates one example of the reference trajectory database.

TABLE 1

| Motion | Time | X | Y | Z |
|---|---|---|---|---|
| Motion1 | $t = [t_1 : t_{N1}]$ | $x_1(t)$ | $y_1(t)$ | $z_1(t)$ |
| Motion2 | $t = [t_2 : t_{N2}]$ | $x_2(t)$ | $y_2(t)$ | $z_2(t)$ |
| ... | ... | ... | ... | ... |

Referring to Table 1, each motion is a function of the sub-motion along two or three axis x, y, z, depending on whether two- or three-dimensional coordinates are employed. The coordinate axes may be defined by using the user's 106 torso or the mass centre as the origin, x-axis may be a forward-backward axis, y-axis may be the lateral axis, and z-axis may be vertical axis. This has the advantage in that the local motion data is also defined as motion with respect to the torso or mass centre. As a consequence, the local motion data and the axes of the reference trajectory database are inherently in the same coordinates. Now, the local motion data acquired in the above-described manner may be divided into the two or three components each associated with a different axis of the coordinates, and the comparison between the reference motion trajectories may be carried out per axis.

In addition or as an alternative to using the reference trajectory database in determining the sports type, the reference trajectory database may be used in evaluating the user's 106 performance in the apparatus. In an embodiment, at least some of the reference motion trajectories stored in the database are motion trajectories that the user 106 should be able to repeat or to avoid. Some reference motion trajectories may be model trajectories representing the correct technique while other reference motion trajectories may be model trajectories representing performance under fatigue or erroneous trajectories. In an embodiment, the apparatus is configured to monitor the user's performance by analysing the motion trajectories performed by the user from the local motion data. The apparatus may compare the local motion data with the reference motions and determine the user's 106 performance on the basis of the comparison. In an embodiment, the apparatus may output the result of the performance evaluation to the user via a user interface of the apparatus. For example, if the apparatus has been provided or it has determined the sports type the user is currently performing, if the apparatus detects that the local motion performed by the user cannot be mapped to one or more of the reference motion trajectories associated with the sports type in the reference trajectory database, the apparatus may output a notification about correcting the technique. If the apparatus detects from the local motion data that the local motion performed by the user 106 is mapped to a reference motion trajectory associated with the fatigue, the apparatus may output a notification that the user should take a rest.

In an embodiment alternative to blocks 702, 704 of FIG. 7 the determined type of locomotion may be used to configure other signal processing applied to the measurement data. For example, an energy expenditure estimation algorithm may be selected on the basis of the type of locomotion determined in block 700. As known, a different energy expenditure estimation algorithm may be applied for running, walking, swimming, and any other sports type. Each type of locomotion may exert the user 106 in a different manner and, thus, affect the energy expenditure. Using a correct energy expenditure estimation algorithm matched to the type of locomotion enables more accurate energy expenditure estimates. In an embodiment, a metabolic equivalent of task (MET) value is selected on the basis of the determined sports type. One MET may be defined as 1 kcal/(kg*h) wherein kcal refers to kilocalories, kg to kilograms, and h to an hour. One MET is typically expended when sitting still. Two-to-four METs is expended when walking, and seven-to-ten METs is expended when running. This embodiment enables fast change of the MET used in the energy expenditure estimation algorithm when the type of locomotion changes. As a consequence, the energy expenditure estimates remain accurate.

In yet another embodiment alternative to blocks 702 and 704, the type of locomotion determined in block 700 may be used to configure the satellite positioning receiver. In this embodiment, a sampling frequency of the satellite positioning receiver is determined on the basis of the type of locomotion. For example, when the type of locomotion is determined to be periodic or rhythmic such as walking or running, the sampling frequency may be decreased, e.g. to 1 Hz or 2 Hz. On the other hand, when the type of locomotion is determined to be spurious, a higher sampling frequency may be selected, e.g. 10 Hz.

Figure 8:
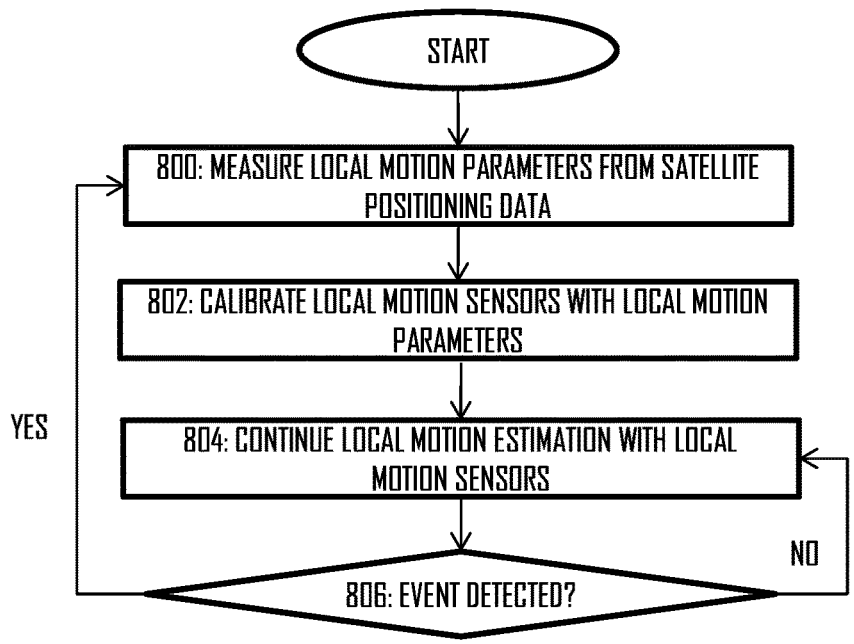
FIG. 8 illustrates a process for using satellite positioning data to calibrate motion sensors according to an embodiment of the invention.

In an embodiment, other motion sensors may be employed together with the satellite positioning receiver to measure the local motion of the user 106. The other motion sensors may comprise at least one of the following: at least one accelerometer, a three-dimensional accelerometer, a gyroscope, and a magnetometer. In some embodiments, a plurality of the above-listed sensors is employed. In an embodiment, a sensor fusion comprising a three-dimensional accelerometer, a gyroscope, and a magnetometer is employed. In an embodiment, the satellite positioning data is used to calibrate the motion sensors other than the satellite positioning receiver. FIG. 8 illustrates a process for calibrating the motion sensor(s) according to an embodiment of the invention. Referring to FIG. 8, the apparatus measures parameters of the local motion from the satellite positioning data (block 800), e.g. from the local motion data acquired from the satellite positioning data. Block 800 may comprise measuring a motion trajectory along each of the above-mentioned two or three axes over one or more periods of periodic motion. After measuring the parameters of the local motion in block 800, the local motion parameters may be used in calibrating the one or more motion sensors other than the satellite positioning receiver (block 802). In an embodiment, block 802 comprises modifying measurement data provided by the one or more other motion sensors with the parameters. For example, as the parameters acquired in block 800 are inherently bound to the determined coordinates, the measurement data provided by the one or more other motion sensors may be mapped to the same coordinates by using a weighting function determined from the difference between the local motion data acquired in block 800 and the measurement data acquired from the one or more other sensors. For example, the gyroscope is known to be in need of repeated calibration because of drifting. The local motion data acquired from the satellite positioning data may be used to bind the measurement data provided by the gyroscope to the same coordinates to which the local motion data is associated. A basic assumption may be that the user is performing the same periodic motion during block 800 and during blocks 802 and 804. In block 804, the local motion estimation is continued by using the one or more other sensors after they have been calibrated. During the execution of block 804, the satellite positioning receiver may be shut down or put to a power-save mode.

The one or more other motion sensors may be recalibrated upon detecting a determined event (block 806). The event may be a time-based event, e.g. the recalibration may be performed after a determined time interval has elapsed from the previous execution of block 802. The event may detected from the measurement data provided by the one or more motion sensors. For example, when the apparatus determined on the basis of the measurement data that the motion trajectory has changed, the apparatus may carry out recalibration. In the recalibration, the process may reiterate blocks 800 and 802 and, then, continue the execution of block 804 with the newly calibrated motion sensors.

Figure 9:
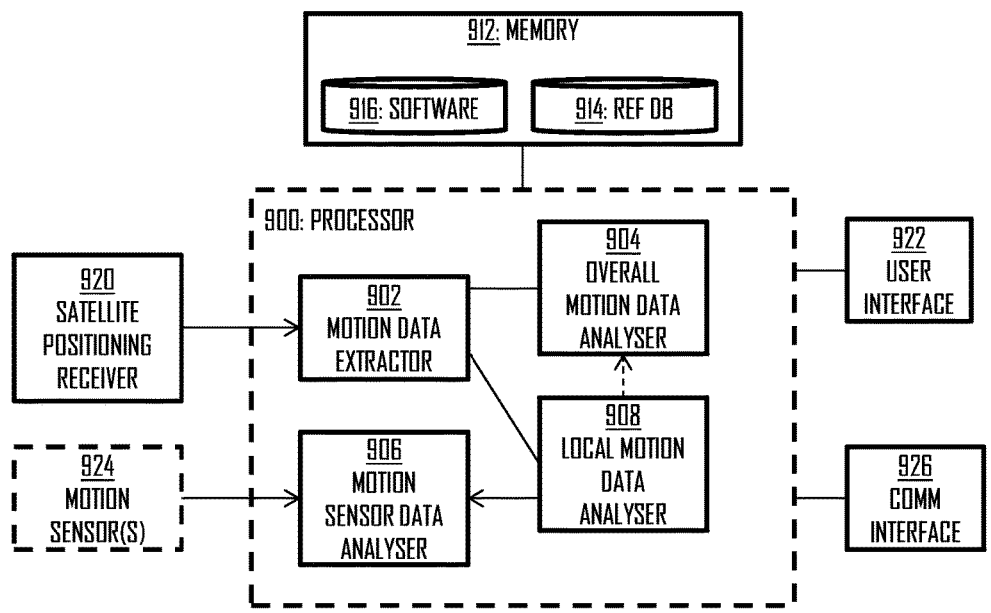
FIGS. 9 and 10 illustrate block diagrams of apparatuses according to some embodiments of the invention.
Figure 10:
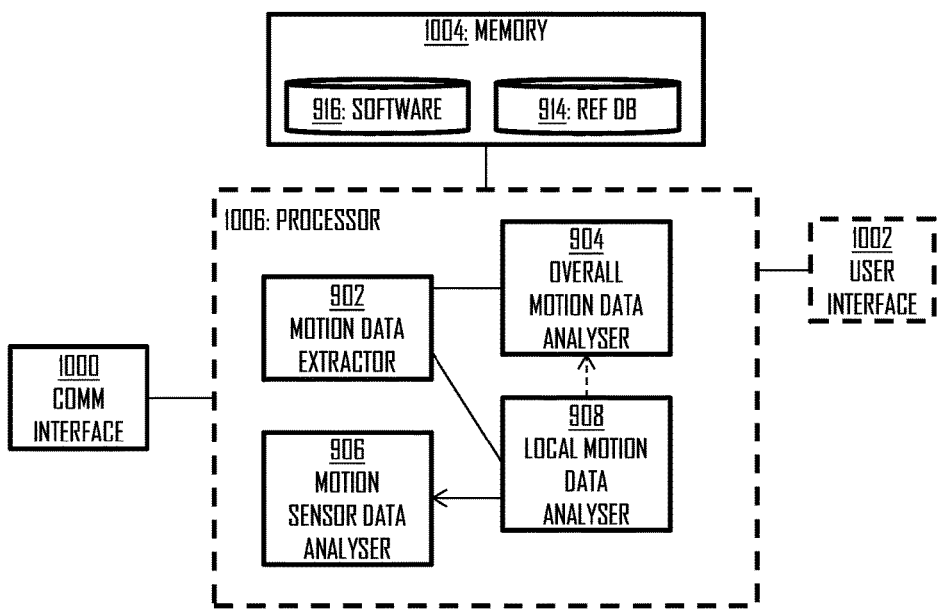

FIGS. 9 and 10 illustrate block diagrams of some embodiments of the above-mentioned apparatus configured to execute the procedures and functions described above in connection with FIGS. 1 to 8. In the embodiment of FIG. 9, the apparatus may be the training computer 100 arranged to be worn by the user 106 during the physical exercise. The apparatus may be the above-mentioned wrist computer, for example. In the embodiment of FIG. 10, the apparatus may be a server computer connected to the Internet and configured to process and store personal training data including measurement data of a plurality of users. In both embodiments, the apparatus comprises at least one processor and at least one memory storing a computer program code, wherein the at least one memory and the computer program code are configured, with the at least one processor, to cause the apparatus to perform the processing of the satellite positioning data in the above-described manner. According to another aspect, the at least one memory and the computer program code are configured, with the at least one processor, to process the satellite positioning data in the above-described manner.

Referring to FIG. 9, the apparatus comprises a satellite positioning receiver 920 arranged to acquire the above-described satellite positioning data on the basis of signals received from a plurality of positioning satellites. The satellite positioning receiver 920 may acquire positioning coordinates as the satellite positioning data and output the positioning coordinates to a processor 900. The processor 900 may comprise a motion data extractor circuitry 902 configured to extract the above-described local motion data and the overall motion data from the satellite positioning data. The motion data extractor circuitry 902 may extract the local motion data and the overall motion data from the positioning coordinates that indicate spatial displacement, or the motion data extractor circuitry 902 may convert the positioning coordinates to speed values. In the embodiment using the speed values, the speed values may be computed from the positioning coordinates by using a short averaging window or even no averaging window. Upon extracting the local motion data and the overall motion data, the motion data extractor may output the local motion data to a local motion data analyser 908 and the overall motion data to an overall motion data analyser 904. The local motion data analyser 908 may estimate the local motion by performing the above-described functions, e.g. determine the sports type, evaluate whether or not the local motion is periodic, evaluate performance of the user by analysing trajectories of the local motion data, etc. The overall motion data analyser 904 may estimate the motion of the whole human body from the overall motion data, e.g. overall speed of the user 106 by estimating the speed from the overall motion data. The local motion data analyser 908 may provide the overall motion data analyser 904 with a length of an averaging window used for computing the speed, as described above.

In some embodiments, the apparatus comprises the one or more motion sensors 924 described above, e.g. one or more sensors other than the satellite positioning receiver 920. The motion sensor(s) 924 may comprise one or more of the above-described motion sensors and be configured to measure motion of the user 106 and output measurement data to the processor 900. The measurement data may comprise translational acceleration measurement data provided by one or more accelerometers, rotational measurement data provided by a gyroscope, and/or magnetic measurement data provided by a magnetometer. The processor 900 may comprise a motion sensor data analyser 906 configured to process the measurement data and determine the user's motion trajectories from the measurement data received from the motion sensor(s) 924. In an embodiment of FIG. 8, the local motion analyser may be configured to determine the local motion parameters from the local motion data and output the parameters to the motion sensor data analyser 906. The motion sensor data analyser 906 may then use the parameters to calibrate the measurement data received from the motion sensors 924, as described above.

The apparatus may further comprise a memory 912 storing a computer program code 916 comprising program instructions defining the functions executed by the sub-circuitries 902 to 908 of the processor 900. The memory 912 may further store the above-described reference trajectory database 914. The apparatus may further comprise a user interface 922 comprising a display unit and at least one input device. The display unit may be configured to display information acquired as a result of the processing performed by the analysers 904, 906, 908 such as the speed of the overall motion, the speed of the local motion, an output indicating the user's performance in carrying out the motion trajectories, and/or instructions derived from the processing performed by the analysers 904, 906, 908. The input device may comprise one or more buttons and/or a touch-sensitive panel. The apparatus may further comprise a communication interface 926 providing the apparatus with wired and/or wireless communication capability with other apparatuses. The communication interface 926 may provide a communication connection with a heart rate transmitter configured to measure the user's 106 heart rate from the user's 106 chest, for example. The heart rate transmitter may be a strap arranged to be attached around the chest. The communication connection may be established by using Bluetooth wireless communication technology, induction-based communication technology, or ANT or ANT+ communication technology. The communication interface 926 may further provide a communication connection with a computer such as the server computer or a personal computer operating as a client computer with respect to the server computer. The communication interface 926 may be used by the processor 900 to transfer training data from the apparatus to the computer. The training data may comprise training data acquired as a result of the processing performed by the sub-circuitries 904, 906, 908 of the processor 900. The training data may comprise the local motion trajectories performed by the user 106, recorded speed values of the local motion and/or the overall motion, etc.

The apparatus may further comprise or be connected to a heart activity sensor arranged to measure heart activity of the user 106 and process the measured heart activity. The heart activity sensor may be based on measuring electrocardiogram, or it may be based on optical heart activity sensing. In the embodiments where the apparatus is connected to the heart activity sensor, the heart activity sensor may be provided in a separate casing than a casing housing the apparatus, and a wireless connection may be established between the heart activity sensor and the apparatus. The connection may be a Bluetooth connection, for example.

Referring to FIG. 10, the apparatus employed in the server computer may comprise a communication interface 1000 providing communication connection to a communication network through which the above-described training data may be received. In some embodiments, the communication interface 1000 may be employed to receive the above-described satellite positioning data acquired by the satellite positioning receiver 920 and the measurement data measured by the motion sensor(s) 924 attached to the user 106 during the physical exercise. Such data may be received in the apparatus of FIG. 10 in real time during the physical exercise and/or after the physical exercise. The apparatus may comprise a processor 1006. The processor 1006 may comprise the same or similar sub-circuitries 902 to 908 as the apparatus of FIG. 9 and enable the processor 1006 to perform the above-described functions with respect to the processing of the satellite positioning data. The apparatus may comprise a memory 1004 storing a computer program code 916 configuring the sub-circuitries 902 to 906 to perform at least some of the functions above-described above in connection with FIGS. 1 to 8. The memory may further store the reference trajectory database 914 and, in some embodiments, a training database storing exercise profiles and measurement data recorded from the physical exercises performed by the user 106 and other users. The apparatus may further comprise a user interface 1002 comprising a display unit, a keyboard, etc.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in connection with FIGS. 1 to 8 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

Some embodiments of the invention are described above in connection with FIGS. 1 to 8. However, further embodiments may be developed from these embodiments, as the technology evolves. Such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A method comprising:
acquiring, in an apparatus, using a satellite positioning receiver or a communication interface, satellite positioning data received with a satellite positioning receiver attached to a human body and indicating a location of the satellite positioning receiver;
extracting, by the apparatus, using a motion data extractor, from the satellite positioning data, local motion data representing local motion of the satellite positioning receiver with respect to a reference point and overall motion data representing the motion of the reference point, wherein the reference point is comprised in a framework of the human body; and
determining, using a motion analyzer, from the local motion data, a local motion trajectory of a part of a human body to which the satellite positioning receiver is attached, the local motion trajectory being determined with respect to the reference point comprised in the trajectory of the human body, wherein the overall motion data is acquired by averaging the satellite positioning data over an observation interval, and wherein the local motion data is acquired by subtracting the overall motion data from the satellite positioning data.

2. The method of claim 1, wherein the local motion data represents local motion of a limb of the human body.

3. The method of claim 1, further comprising:
determining whether or not the local motion data is periodic;
upon determining that the local motion data is periodic, splitting the local motion data into a plurality of subsets of local motion data samples, wherein each subset consists of local motion data samples over one period, and wherein different subsets are associated with different periods;
averaging local motion data samples of the different subsets, wherein the averaged local motion data samples have the same time index within the period; and
acquiring, as a result, averaged local motion data representing averaged periodic motion of the part of the human body.

4. The method of claim 1, further comprising identifying a type of locomotion of the human body from the local motion data.

5. The method of claim 4, further comprising:
providing a mapping table mapping each type of locomotion to an averaging window used to acquire the overall motion data from the satellite positioning data;
selecting, on the basis of the identified sports type, an averaging window mapped to the identified type of locomotion; and
using the selected averaging window to acquire the overall motion data from the satellite positioning data.

6. The method of claim 1, further comprising determining at least one of step cadence, step length, and step count from the local motion data.

7. The method of claim 1, further comprising using at least one of local motion data and the overall motion data acquired from the satellite positioning data to calibrate at least one motion sensor other than the satellite positioning receiver.

8. The method of claim 7, wherein the at least one motion sensor comprises at least one of the following: at least one accelerometer, a gyroscope, and a magnetometer.

9. A method comprising:
- acquiring, in an apparatus, using a satellite positioning receiver or a communication interface, satellite positioning data received with a satellite positioning receiver attached to a human body and indicating a location of the satellite positioning receiver;
- extracting, by the apparatus, using a motion data extractor, from the satellite positioning data, local motion data representing local motion of the satellite positioning receiver with respect to a reference point and overall motion data representing the motion of the reference point, wherein the reference point is comprised in a framework of the human body; and
- determining, using a motion analyzer, from the local motion data, a local motion trajectory of a part of a human body to which the satellite positioning receiver is attached, the local motion trajectory being determined with respect to the reference point comprised in the trajectory of the human body, wherein the overall motion data is acquired by averaging the satellite positioning data over an observation interval, and wherein the local motion data is acquired by subtracting the overall motion data from the satellite positioning data.

10. The method of claim 9, wherein the signature points are determined by monitoring for a determined pattern in inertial measurement data provided by at least one inertial sensor and, upon detecting the determined pattern in the inertial measurement data, marking at least one sample of the satellite positioning data having the same timing with the detection of the determined pattern.

11. A method comprising:
- acquiring, in an apparatus, using a satellite positioning receiver or a communication interface, satellite positioning data received with a satellite positioning receiver attached to a human body and indicating a location of the satellite positioning receiver;
- extracting, by the apparatus, using a motion data extractor, from the satellite positioning data, local motion data representing local motion of the satellite positioning receiver with respect to a reference point and overall motion data representing the motion of the reference point, wherein the reference point is comprised in a framework of the human body;
- determining, using a motion analyzer, from the local motion data, a local motion trajectory of a part of a human body to which the satellite positioning receiver is attached, the local motion trajectory being determined with respect to the reference point comprised in the trajectory of the human body;
- using at least one of local motion data and the overall motion data acquired from the satellite positioning data to calibrate at least one motion sensor other than the satellite positioning receiver;
- acquiring motion parameters characterizing a local motion trajectory from the local motion data;
- calibrating motion sensor data measured with the at least one motion sensor with the acquired motion parameters; and
- continuing measurements with the at least one calibrated motion sensor while shutting down the satellite positioning receiver.

12. The method of claim 11, further comprising recalibrating the at least one motion sensor with the local motion data of the satellite positioning data upon detecting a determined event.

13. An apparatus comprising:
- at least one processor; and
- at least one memory including a computer program code, wherein the at least one memory and the computer program code are configured, with the at least one processor, to cause the apparatus to perform operations comprising:
  - acquiring, by the apparatus, from a satellite positioning receiver or a communication interface, satellite positioning data received with a satellite positioning receiver attached to a human body and indicating a location of the satellite positioning receiver;
  - extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body;
  - determining, by the apparatus, from a motion analyzer, from the local motion data, a local motion trajectory of a part of a human body to which the satellite positioning receiver is attached, the local motion trajectory being determined with respect to the reference point comprised in the trajectory of the human body; and
  - acquiring, by the apparatus, the overall motion data by marking determined signature points of the satellite positioning data according to a determined criterion and by determining the overall motion data from motion of the marked signature points.

14. The apparatus of claim 13, wherein the local motion data represents local motion of a limb of the human body.

15. The apparatus of claim 13, wherein the operations further comprise:
- determining whether or not the local motion data is periodic;
- upon determining that the local motion data is periodic, splitting the local motion data into a plurality of subsets of local motion data samples, wherein each subset consists of local motion data samples over one period, and wherein different subsets are associated with different periods; and
- averaging local motion data samples of the different subsets, wherein the averaged local motion data samples have the same time index within the period and acquiring, as a result, averaged local motion data representing averaged periodic motion of the part of the human body.

16. The apparatus of claim 13, wherein the operations further comprise identifying a type of locomotion of the human body from the local motion data.

17. The apparatus of claim 16, wherein the operations further comprise:
- providing a mapping table mapping each type of locomotion to an averaging window used to acquire the overall motion data from the satellite positioning data;
- selecting, on the basis of the identified sports type, an averaging window mapped to the identified type of locomotion; and
- using the selected averaging window to acquire the overall motion data from the satellite positioning data.

18. The apparatus of claim 13, wherein the operations further comprise determining at least one of step cadence, step length, and step count from the local motion data.

19. The apparatus of claim 13, wherein the operations further comprise using at least one of local motion data and the overall motion data acquired from the satellite positioning data to calibrate at least one motion sensor other than the satellite positioning receiver.

20. The apparatus of claim 19, wherein the at least one motion sensor comprises at least one of the following: at least one accelerometer, a gyroscope, and a magnetometer.

21. An apparatus comprising:
at least one processor; and
at least one memory including a computer program code, wherein the at least one memory and the computer program code are configured, with the at least one processor, to cause the apparatus to perform operations comprising:
acquiring, by the apparatus, from a satellite positioning receiver or a communication interface, satellite positioning data received with a satellite positioning receiver attached to a human body and indicating a location of the satellite positioning receiver;
extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body;
determining, by the apparatus, from a motion analyzer, from the local motion data, a local motion trajectory of a part of a human body to which the satellite positioning receiver is attached, the local motion trajectory being determined with respect to the reference point comprised in the trajectory of the human body; and
acquiring, by the apparatus, the overall motion data by marking determined signature points of the satellite positioning data according to a determined criterion and by determining the overall motion data from motion of the marked signature points.

22. The apparatus of claim 21, wherein the operations further comprise determining the signature points by monitoring for a determined pattern in inertial measurement data provided by at least one inertial sensor and, upon detecting the determined pattern in the inertial measurement data, marking at least one sample of the satellite positioning data having the same timing with the detection of the determined pattern.

23. An apparatus comprising:
at least one processor; and
at least one memory including a computer program code, wherein the at least one memory and the computer program code are configured, with the at least one processor, to cause the apparatus to perform operations comprising:
acquiring, by the apparatus, from a satellite positioning receiver or a communication interface, satellite positioning data received with a satellite positioning receiver attached to a human body and indicating a location of the satellite positioning receiver;
extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body; and
determining, by the apparatus, from a motion analyzer, from the local motion data, a local motion trajectory of a part of a human body to which the satellite positioning receiver is attached, the local motion trajectory being determined with respect to the reference point comprised in the trajectory of the human body;
using, by the apparatus, at least one of local motion data and the overall motion data acquired from the satellite positioning data to calibrate at least one motion sensor other than the satellite positioning receiver;
acquiring, by the apparatus, motion parameters characterizing a local motion trajectory from the local motion data;
calibrating, by the apparatus, motion sensor data measured with the at least one motion sensor with the acquired motion parameters; and
continuing, by the apparatus, measurements with the at least one calibrated motion sensor while shutting down the satellite positioning receiver.

24. The apparatus of claim 23, wherein the operations further comprise recalibrating the at least one motion sensor with the local motion data of the satellite positioning data upon detecting a determined event.

25. A computer program product embodied on a non-transitory distribution medium readable by a computer and comprising program instructions which, when executed by an apparatus, perform a computer process comprising:
acquiring, by the apparatus, from a satellite positioning receiver or a communication interface, satellite positioning data received with a satellite positioning receiver attached to a human body and indicating a location of the satellite positioning receiver;
extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body; and
determining, by the apparatus, from a motion analyzer, from the local motion data, a local motion trajectory of a part of a human body to which the satellite positioning receiver is attached, the local motion trajectory being determined with respect to the reference point comprised in the trajectory of the human body, wherein the overall motion data is acquired by averaging the satellite positioning data over an observation interval, and wherein the local motion data is acquired by subtracting the overall motion data from the satellite positioning data.

26. A computer program product embodied on a non-transitory distribution medium readable by a computer and comprising program instructions which, when executed by an apparatus, perform a computer process comprising:
acquiring, by the apparatus, from a satellite positioning receiver or a communication interface, satellite positioning data received with a satellite positioning receiver attached to a human body and indicating a location of the satellite positioning receiver;
extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body; and
determining, by the apparatus, from a motion analyzer, from the local motion data, a local motion trajectory of a part of a human body to which the satellite positioning receiver is attached, the local motion trajectory being determined with respect to the reference point comprised in the trajectory of the human body, wherein the overall motion data is acquired by marking determined signature points of the satellite positioning data according to a determined criterion and by determining the overall motion data from motion of the marked signature points.

27. A computer program product embodied on a non-transitory distribution medium readable by a computer and comprising program instructions which, when executed by an apparatus, perform a computer process comprising:

acquiring, by the apparatus, using a satellite positioning receiver or a communication interface, satellite positioning data received with a satellite positioning receiver attached to a human body and indicating a location of the satellite positioning receiver;

extracting, by the apparatus, from a motion data extractor, from the satellite positioning data, local motion data representing local motion of the satellite positioning receiver with respect to a reference point and overall motion data representing the motion of the reference point, wherein the reference point is comprised in a framework of the human body;

determining, by the apparatus, from a motion analyzer, from the local motion data, a local motion trajectory of a part of a human body to which the satellite positioning receiver is attached, the local motion trajectory being determined with respect to the reference point comprised in the trajectory of the human body;

using, by the apparatus, at least one of local motion data and the overall motion data acquired from the satellite positioning data to calibrate at least one motion sensor other than the satellite positioning receiver;

acquiring, by the apparatus, motion parameters characterizing a local motion trajectory from the local motion data;

calibrating, by the apparatus, motion sensor data measured with the at least one motion sensor with the acquired motion parameters; and continuing, by the apparatus, measurements with the at least one calibrated motion sensor while shutting down the satellite positioning receiver.

* * * * *